United States Patent [19]

Kamijo et al.

[11] Patent Number: 5,073,553

[45] Date of Patent: Dec. 17, 1991

[54] 3-ALKOXY SUBSTITUTED BENZOFURO[3,2-C]QUINOLIN-6-ONE COMPOUNDS

[75] Inventors: Tetsuhide Kamijo; Arao Ujiie; Naoyuki Tsutsumi; Atsushi Tsubaki, all of Nagano, Japan

[73] Assignee: Kissei Pharmaceutical Co., Ltd., Nagano, Japan

[21] Appl. No.: 440,069

[22] Filed: Nov. 22, 1989

[30] Foreign Application Priority Data

Nov. 22, 1988 [JP] Japan ................................. 63-295715
Nov. 22, 1988 [JP] Japan ................................. 63-295716

[51] Int. Cl.$^5$ ................. A61K 31/535; C07D 413/00
[52] U.S. Cl. ................. 514/232.8; 514/285; 544/125; 546/62
[58] Field of Search ............ 546/62; 544/125, 361; 514/285, 232.8, 255

[56] References Cited

U.S. PATENT DOCUMENTS 5,023,261  6/1991  Kamijo et al. .................... 514/285

OTHER PUBLICATIONS

Advanced Tissue Cultures for In Vitro Assay and Production, pp. 103-115 (1985), Edited by Isao Yamane & Hiroyoshi Endo.
El-Manah et al., "Potent. Non-Ster. Estrogen and Anti Estrog. Synthesis", Croatica Chemica Acta, 59(1), 171-6 (1986).
Yamaguchi et al., "Synth. Benzofuroquinolines", Hetocyclic Chem., 21, pp. 737-739 (1984).

Primary Examiner—Robert T. Bond
Assistant Examiner—Jyothsna Venkat
Attorney, Agent, or Firm—Sughrue, Mion, Zinn, Macpeak & Seas

[57] ABSTRACT

Benzofuro[3,2-c]quinoline compounds of the formula:

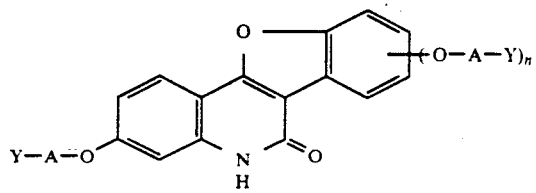

wherein A represents a group of the formula of $-CH_2)_m$ or $-CH_2CH(OH)CH_2-$; Y represents an N,N-dialkylamino group, an N-mono-alkylamino group or a nitrogen atom-containing aliphatic geterocyclic group; n represents 0 or 1; m represents an integer of from 1 to 3, and pharmaceutically acceptable acid addition salts thereof, possess a strong inhibitory action on bone resorption, a stimulatory effect on ossification.

14 Claims, No Drawings

3-ALKOXY SUBSTITUTED BENZOFURO[3,2-C]QUINOLIN-6-ONE COMPOUNDS

FIELD OF THE INVENTION

The present invention relates to benzofuro[3,2-c]quinoline compounds which are useful as a therapeutic agent. More particularly, the present invention relates to novel benzofuro[3,2-c]quinoline compounds represented by the general formula:

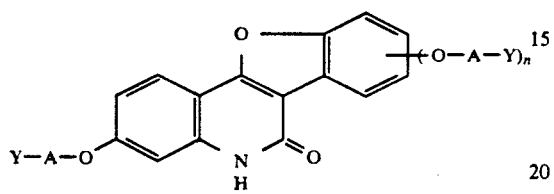

wherein A represents a group of the formula of $-(CH_2)_m-$ or $-CH_2CH(OH)CH_2-$; Y represents an N,N-di-alkylamino group, an N-mono-alkylamino group or a nitrogen atom-containing aliphatic heterocyclic group; n represents 0 or 1; m represents an integer of from 1 to 3, and pharmaceutically acceptable acid addition salts thereof.

BACKGROUND OF THE INVENTION

Osteoporosis is a diseased condition or illness wherein the quantitative loss of bones has progressed beyond a certain limit with no substantial change in chemical composition of the bones. A decrease in the amount of protein, calcium and phosphorus in bones is its physiological feature. Osteoporosis is increased with aging, and is observed most commonly in the elderly. The disease usually invades the vertebrae, and induces dorsal lumbago and shortening of the height. Especially, in the advanced case, the disease invades the long bones. Therefore, fracture often occurs in patients suffering from osteoporosis. It is thought that the femoral fractures observed in old women and men is almost always caused by osteoporosis. Pathogenic factors in the disease are varied, including endocrine disorder and nutritional disorder. Therapeutic agents such as vitamine $D_3$, calcium preparations, calcitonin, and phosphorus preparations are employed in the prevention or treatment of osteoporosis, but these are limited in effect to a given subject and can hardly be expected to show a definite effect on osteoporosis. Therefore, it has long been desired to develop a pharmaceutical agent having a significant effect.

Recently, it has been reported that a certain compound of 3-phenyl-4H-1-benzopyran-4-ones which is different from the above agents is useful as a therapeutic agent for the prevention or treatment of osteoporosis in Japanese Patent Publication No. 13391/79 and Japanese Patent Application (OPI) Nos. 48924/85, 54379/85, 132917/85, 132976/85. (The term "OPI" as used herein refers to an unexamined Japanese patent application).

Up to now, with regard to benzofuro[3,2-c]quinoline compounds related to those of the present invention, the compounds represented by the following formulae (A) and (B) have been disclosed in Bulletin of the Chemical Society of Japan, Vol. 53, pages 1057-1060 (1980), Journal of Heterocyclic Chemistry, Vol. 21, pages 737-739 (1984).

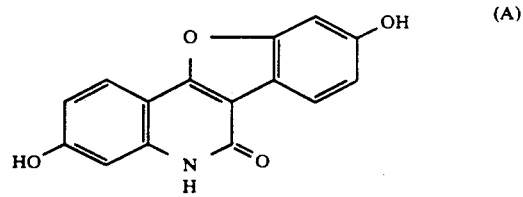

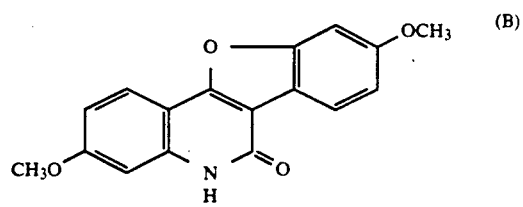

These compounds were prepared in order to investigate their chemical reactivities and to test their activities as mutagens, carcinogens, and anti-tumor substances, but there is no specific disclosure as to their pharmacological activities in these references.

The compounds represented by the above formula (A) and the following formulae (C), (D) and (E) have been disclosed in CROATCA CHEMICA ACTA, Vol. 59, No. 1, pages 171-176 (1986).

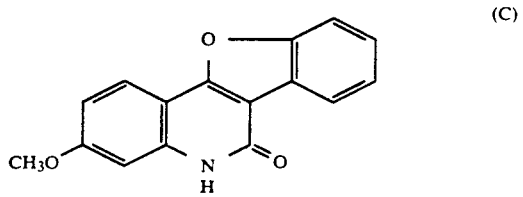

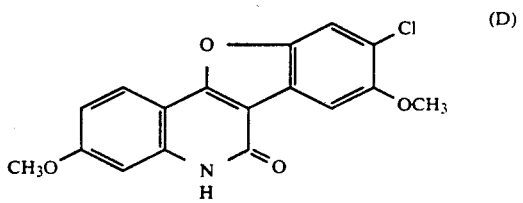

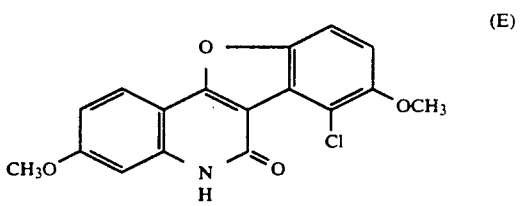

This reference discloses a method for preparation of only compound (C). But there is no specific disclosure as to its pharmacological activity.

Furthermore, it has not been reported in any literature references that any of benzofuro[3,2-c]quinoline compounds is useful for the prevention or treatment of osteoporosis.

The present inventors have investigated to find effective drugs for the prevention or treatment of osteoporosis. As a result, the inventors have found that certain compounds of benzofuro[3,2-c]quinoline compounds and pharmaceutically acceptable acid addition salts thereof exhibit a strong inhibitory action on bone resorption and a stimulatory effect on ossification, and thus that they are useful as therapeutic agents for the prevention and treatment of osteoporosis.

Furthermore, the inventors have found that the compounds of the present invention also exhibit a strong stimulatory effect on longitudinal bone growth. Therefore, they are more useful as the therapeutic agent stated above.

CROSS REFERENCE

Some inventors of the present invention also have filed U.S. patent applications Ser. Nos. 198,270 and U.S. Pat. No. 5,023,261 regarding to benzofuro [3,2-c]quinoline compounds related to those of the present invention.

SUMMARY OF THE INVENTION

An object of the present invention is to provide novel benzofuro[3,2-c]quinoline compounds and pharmaceutically acceptable acid addition salts thereof which exhibit a strong inhibitory action on bone resorption and stimulatory effects on ossification and longitudinal bone growth.

Another object of the present invention is to provide pharmaceutical compositions comprising a benzofuro[3,2-c]quinoline compound or pharmaceutically acceptable acid addition salts thereof.

Other objects, features and advantages of the present invention will be apparent from the following description of the invention.

DETAILED DESCRIPTION OF THE INVENTION

The present invention provides the benzofuro[3,2-c]quinoline compounds and pharmaceutically acceptable acid addition salts thereof which exhibit an inhibitory action on bone resorption and a stimulatory effect on ossification. Furthermore, benzofuro[3,2-c]-quinoline compounds of the present invention exhibit a stimulatory effect on longitudinal bone growth.

Thus, the benzofuro[3,2-c]quinoline compounds and pharmaceutically acceptable acid addition salts thereof of the present invention are useful as therapeutic agents for the prevention or treatment of osteoporosis.

The term "alkyl group" as used herein means a straight- or branched-chain alkyl group having 1 to 6 carbon atoms.

The term "nitrogen atom-containing aliphatic heterocyclic group" as used herein means an aliphatic heterocyclic group which contains at least one ring nitrogen atom and which is 5- or 6- membered ring, such as a morpholino group, a 1-pyrrolidinyl group, a piperidino group and a 4-alkyl-piperazinyl group.

The benzofuro[3,2-c]quinoline compounds of the present invention are characterized by the presence of at least one substituent at the 3-position on the ring, which are selected from a group of the formula of Y—A—O— in which A represents a group of the formula of —CH$_2$)$_m$ or —CH$_2$CH(OH)CH$_2$—; Y represents an N,N-di-alkylamino group, an N-mono-alkylamino group or a nitrogen atom-containing aliphatic heterocyclic group; and m represents an integer of from 1 to 3.

Of the benzofuro[3,2-c]quinoline compounds of the present invention, 3-(2-dimethylaminoethoxy)-5H-benzofuro[3,2-c]quinolin-6-one, 3-(3-morpholino-2-hydroxypropoxy)-5H-benzofuro[3,2-c]quinolin-6-one, 3-(2-diethylaminoethoxy)-5H-benzofuro[3,2-c]quinolin-6-one, 3-(3-isopropylamino-2-hydroxypropoxy)-5H-benzofuro[3,2-c]quinolin-6-one are preferable. Especially, 3-(2-dimethylaminoethoxy)-5H-benzofuro[3,2-c]quinolin-6-one is the most preferable.

The benzofuro[3,2-c]quinoline compounds of the present invention can be prepared according to methods known per se. That is, the benzofuro[3,2-c]quinoline compounds of the present invention represented by the general formula (I):

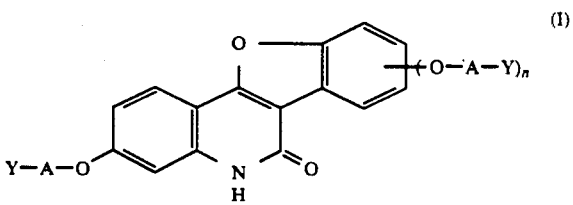

wherein A represents a group of the formula of —CH$_2$)$_m$ or —CH$_2$CH(OH)CH$_2$—; Y represents an N,N-di-alkylamino group, an N-mono-alkylamino group or a nitrogen atom-containing aliphatic heterocyclic group; n represents 0 or 1; and m represents an integer of from 1 to 3 can be prepared from the compounds represented by the general formula (II):

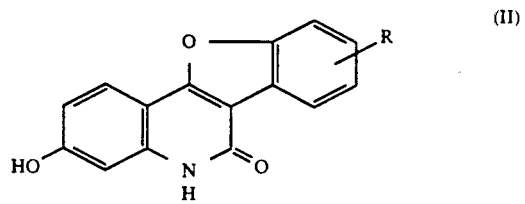

wherein R represents a hydrogen atom or a hydroxy group.

That is, of the compounds represented by the general formula (I) of the present invention, the compounds represented by the general formula (Ia):

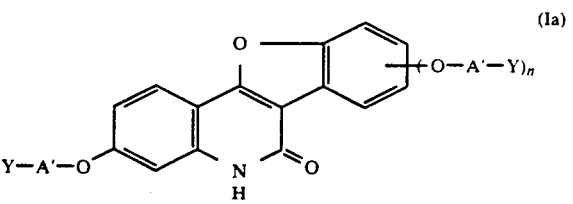

wherein A' represents a group of the formula of —(CH$_2$)$_m$; Y, m, and n have the same meanings as defined above, can be prepared by reacting a compound represented by the general formula (II) with a compound represented by the general formula (III):

Y—A'—X       (III)

wherein X represents a halogen atom; and A' and Y have the same meanings as defined above, in the presence of a basic substance such as sodium bicarbonate, potassium carbonate and sodium hydroxide in an inert organic solvent such as N,N-dimethylformamide.

Of the compounds represented by the general formula (I) of the present invention, the compounds represented by the general formula (Ib):

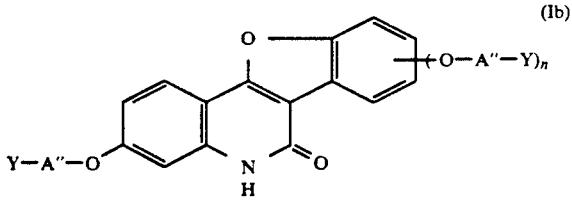

wherein A″ represents a group of the formula of —CH₂CH(OH)CH₂—; Y and n have the same meanings as defined above, can be prepared by reacting the compound represented by the general formula (II) with a compound represented by the general formula (IV):

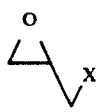

wherein X represents a halogen atom, in the presence of a basic substance such as potassium carbonate and sodium bicarbonate in an inert organic solvent such as N,N-dimethylformamide, and then, by reacting the resulting compound with a compound represented by the general formula (V):

YH  (V)

wherein Y has the same meaning as defined above.

The compounds represented by the general formula (II) used as starting materials in the present invention can be easily prepared by the methods disclosed in the literature, for example, Bulletin of the Chemical Society of Japan, Vol. 53, pages 1057–1060, 1980; Journal of Heterocyclic Chemistry, Vol. 16, pages 487–491, 1979; ibidem, Vol. 21, pages 737–739, 1984 or an analogous method thereto.

The compounds represented by the general formula (III),(IV) and (V) are available commercially.

The desired product can be isolated and purified in a conventional manner such as washing, recrystallization and silica gel column chromatography.

In the benzofuro[3,2-c]quinoline compounds having an asymmetric carbon atom represented by the general formula (I) of the present invention, the configuration of a substituent on the asymmetric carbon atom is not limited particularly. That is, S-configuration, R-configuration or a mixture of S- and R-configuration can be employed in the present invention.

Such optically active compounds represented by the general formula (I) of the present invention can be prepared by performing an optical resolution according to a usual manner or by using optically active starting materials.

The compounds represented by general formula (I) of the present invention can be converted into pharmaceutically acceptable acid addition salts thereof according to a usual manner.

Examples of such salts include a hydrochloric acid salt, a sulfonic acid salt, a p-toluenesulfonic acid salt, an acetic acid salt, a citric acid salt, a succinic acid salt, a tartaric acid salt, a fumaric acid salt and the like.

The benzofuro[3,2-c]quinoline compounds represented by the general formula (I) of the present invention possess a strong inhibitory action on bone resorption and a stimulatory effect on ossification, for example, the benzofuro[3,2-c]quinoline compounds produce a significant effect at a $10^{-5}$ molar concentration when determined by an in vitro experiment using the femur of a chick embryo. Furthermore, some benzofuro[3,2-c]quinoline compounds represented by the general formula (I) of the present invention also possess a stimulatory effect on longitudinal bone growth.

The benzofuro[3,2-c]quinoline compounds of the general formula (I) and the pharmaceutically acceptable acid addition salts thereof of the present invention can be administered in various dosage forms depending upon the intended therapy. Typical dosage forms which can be used are tablets, pills, powders, suspensions, emulsions, granules, capsules, suppositories, and injectable preparations.

In molding the pharmaceutical compositions into a tablet form, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, and ethanol, and disintegrators such as laminaria and agar. The tablets, if desired, can be coated into sugar-coated tablets, gelatin-coated tablets, film-coated tablets, or tablets coated with two or more layers.

When the pharmaceutical composition is formulated into an injectable preparation, the resulting solution and suspension are preferably sterilized, and are isotonic with respect to blood. In making the pharmaceutical composition into a solution or suspension, all diluents customarily used in the art can be employed. Examples of suitable diluents are water, ethyl alcohol, propylene glycol, ethoxylated isostearyl alcohol, polyoxyethylene sorbitol, and sorbitan esters. Sodium chloride, glucose or glycerol can be incorporated into a therapeutic agent in an amount sufficient to prepare an isotonic solution. The therapeutic agent may further contain ordinary dissolving aids, buffers, pain-alleviating agents, and optionally, coloring agents, fragrances, flavors, sweeteners, and other pharmacologically active agents which are known in the art.

The dosage of the benzofuro[3,2-c]quinoline compounds of the present invention can be in the range from about 10 mg to 1,000 mg per adult human by oral administration per day, or from about 1 mg to 100 mg per adult human by parenteral administration per day in multiple doses depending upon the type of disease, the severity of condition to be treated, and the like.

The present invention is further illustrated in more detail by way of the following Examples. The melting points of the products obtained were uncorrected.

EXAMPLE 1

3-(2-Dimethylaminoethoxy)-5H-benzofuro[3,2-c]quinolin-6-one (Compound 1)

In dry N,N-dimethylformamide was dissolved 6.0 g of 3-hydroxy-5H-benzofuro[3,2-c]quinolin-6-one, and 1.1 g of 2-dimethylaminoethyl chloride hydrochloride and 6.02 g of sodium bicarbonate were added to the solution. The mixture was stirred for 16 hours at 120° C. Into the reaction mixture were poured chloroform and water, and the insolved materials were filtered out. The organic layer was washed with water, dried over magnesium sulfate anhydride, and evaporated under reduced pressure. The residue was washed with ether, and recrystallized from chloroform and ethyl acetate to obtain 3.29 g of 3-(2-dimethylaminoethoxy)-5H-benzofuro[3,2-c]quinolin-6-one.

Melting point: 213°–217° C.
IR (KBr): $\nu_{co}$ 1660 cm$^{-1}$
NMR (CDCl$_3$)

δ: 2.40(s, 6H), 2.82(t, 2H), 4.20(t, 2H), 6.90–7.10(m, 2H), 7.35–7.70(m, 3H), 7.98(d, 1H), 8.20–8.35(m, 1H), 11.36(br-s, 1H)

EXAMPLE 2

The following compounds were prepared in a similar manner to that described in example 1 except that 2-morpholinoethyl chloride hydrochloride, N-methyl-3-piperidinylmethyl chloride hydrochloride, 2-(1-pyrrolidinyl)ethyl chloride hydrochloride, 2-diethylaminoethyl chloride hydrochloride or 2-(N-methyl-2-pyrrolidinyl)ethyl chloride hydrochloride were used in place of 2-dimethylaminoethyl chloride hydrochloride.

3-(2-Morpholinoethoxy)-5H-benzofuro[3,2-c]quinolin-6-one (Compound 2)

Melting point: 244°–251° C. (decomp.)
IF (KBr): $\nu_{co}$ 1660 cm$^{-1}$
NMR (DMSO-d$_6$)

δ: 2.50–3.90(m, 10H), 4.25–4.45(m, 2H), 7.10–7.30(m, 2H), 7.50–7.70(m, 2H), 7.90–8.25(m, 3H), 12.00(br-s, 1H)

3-{2-(1-Pyrrolidinyl)ethoxy}-5H-benzofuro[3,2-c]quinolin-6-one (Compound 3)

Melting point: 224°–228° C.
IR (KBr): $\nu_{co}$ 1660 cm$^{-1}$
NMR (DMSO-d$_6$)

δ: 1.70–3.20(m, 10H), 4.32(t, 2H), 7.05–7.25(m, 2H), 7.50–7.70(m, 2H), 7.85–8.25(m, 3H), 12.01(s, 1H)

3-(2-Diethylaminoethoxy)-5H-benzofuro[3,2-c]quinolin-6-one (Compound 4)

Melting point: 202°–204° C.
IR (KBr): $\nu_{co}$ 1660 cm$^{-1}$
NMR (DMSO-d6)

δ: 1.10(t, 6H), 2.70(q, 4H), 2.96(t, 2H), 4.22(t, 2H), 7.05–7.20(m, 2H), 7.50–7.65(m, 2H), 7.85–8.25(m, 3H), 11.97(s, 1H)

EXAMPLE 3

The following compound was prepared in a similar manner to that described in example 1 except that 3,9-dihydroxy-5H-benzofuro[3,2-c]quinolin-6-one was used in place of 3-hydroxy-5H-benzofuro[3,2-c]quinolin-6-one and other reagents were used twice as much.

3,9-(2-Morpholinoethoxy)-5H-benzofuro[3,2-c]-quinolin-6-one (Compound 5)

Melting point: 209°–214° C.
IR (KBr): $\nu_{co}$ 1660 cm$^{-1}$
NMR (CDCl$_3$)

δ: 2.50–2.75(m, 8H), 2.80–2.95(m, 4H), 3.60–3.85 (m, 8H), 4.15–4.30(m, 4H), 6.90–7.20(m, 4H), 7.90–8.10(m, 2H), 10.75(br-s, 1H)

EXAMPLE 4

3-(2-Hydroxy-3-morpholinopropoxy)-5H-benzofuro[3,2-c]quinolin-6-one (Compound 6)

In N,N-dimethylformamide was dissolved 10.0 g of 3-hydroxy-5H-benzofuro[3,2-c]quinolin-6-one, and to the solution were added 28.0 g of epibromohydrin and 5.5 g of potassium carbonate. The mixture was stirred at 55° C. for 3 hours. Into the reaction mixture was poured water, and precipitates were collected by filtration, washed with water, and dried to obtain 11.8 g of 3-(2,3-epoxypropoxy)-5H-benzofuro[3,2-c]quinolin-6-one.

6.0 g of 3-(2,3-epoxypropoxy)-5H-benzofuro[3,2-c]quinolin-6-one obtained was suspended into 100 ml of morpholine, and the mixture was heated for 2 hours at 70° C. Into the reaction mixture was poured water, and extraction with ethyl acetate then performed. The organic layer was washed with water, dried over magnesium sulfate anhydride, and evaporated under reduced pressured to obtain 4.63 g of 3-(2-hydroxy-3-morpholinopropoxy)-5H-benzofuro[3,2-c]quinolin-6-one.

Melting point: 228°–230° C.
IR (KBr): $\nu_{co}$ 1660 cm$^{-1}$
NMR (DMSO-d$_6$)

δ: 2.46–3.55(m, 6H), 3.60–3.75(m, 4H), 4.00–4.30 (m, 3H), 5.13(d, 1H), 7.05–7.20(m, 2H), 7.50–7.65(m, 2H), 7.90–8.25(m, 3H), 11.96 (br-s, 1H)

EXAMPLE 5

The following compounds were prepared in a similar manner to that described in example 4 except that dimethylamine or isopropylamine was used in place of morpholine.

3-(3-Dimethylamino-2-hydroxypropoxy)-5H-benzofuro[3,2-c]quinolin-6-one (Compound 7)

Melting point: 212°–216° C.
IR (KBr): $\nu_{co}$ 1660 cm$^{-1}$
NMR (DMSO-d$_6$)

δ: 2.32(s, 6H), 2.35–2.65(m, 2H), 4.00–4.25(m, 3H), 5.10(br-s, 1H), 7.05–7.20-(m, 2H), 7.50–7.65(m, 2H), 7.90–8.25(m, 3H), 11.96(br-s, 1H)

3-(3-Isopropylamino-2-hydroxy-propoxy)-5H-benzofuro[3,2-c]quinolin-6-one (Compound 8)

Melting point 231°–234° C.
IR (KBr): $\nu_{co}$ 1660 cm$^1$
NMR (DMSO-d$_6$)

δ: 1.10(d, 6H), 2.65–2.90(m, 3H), 3.95–4.25(m, 3H), 5.15–5.25(m, 1H), 7.05–7.20(m, 2H), 7.50–7.65(m, 2H), 7.90–8.25(m, 3H)

EXAMPLE 6

The following compounds were prepared in a similar manner to that described in example 4 except that 3,9-bis(2,3-epoxypropoxy)-5H-benzofuro[3,2-c]quinolin-6-one was used in place of 3-(2,3-epoxypropoxy)-5H-benzofuro[3,2-c]quinolin-6-one and other reagents such as the amino compound were used in an amount of twice as much.

3,9-Bis(2-hydroxy-3-morpholinopropoxy)-5H-benzofuro[3,2-c]quinolin-6-one (Compound 9)

Melting point: 189°–196° C.
IR (KBr): $\nu_{co}$ 1660 cm$^{-1}$
NMR (DMSO-d$_6$)

δ: 2.40–3.80(m, 20H), 4.00–4.30(m, 6H), 5.00–5.15(m, 2H), 7.05–7.25(m, 3H), 7.57(br-s, 1H), 7.95–8.10(m, 2H), 11.92(br-s, 1H)

3,9-Bis(3-isopropylamino-2-hydroxypropoxy)-5Hbenzofuro[3,2-c]quinolin-6-one (Compound 10)

Melting point: 172°–176° C.
IR (KBr): $\nu_{co}$ 1660 cm$^{-1}$
NMR (DMSO-d$_6$)

δ: 1.11(d, 12H), 2.65–2.95(m, 6H), 3.95–4.25(m, 6H), 7.00–7.25(m, 3H), 7.56(br-s, 1H), 7.95–8.10(m, 2H)

EXAMPLE 7

The inhibitory effect on bone resorption

Inhibitory effect of various compounds on bone resorption was tested according to the method described in "Advanced Tissue Cultures For In Vitro Assay And Production" (pages 111-114, edited by Isao Yamane & Hiroyoski Endo, Published by SOFT SCIENCE, Inc. Tokyo).

Femur was isomated from 10- to 11-day old chick embryos. After cleaning off adherent soft tissues, the preparation was precultuvated in 1 ml of BGJb-HW2 culture medium containing benzofuro[3,2-c]quinoline compounds of the present invention at 37° C. for 24 hours using the roller-tube method. Each tested compound was dissolved in dimethylsulfoxide at a concentration of 0.01M and the solution was diluted with the culture medium to make a final concentration of $10^{-5}M$ of those compounds. In the case of control group, the same volume of a dimethylsulfoxide was added.

On the next day, the precultivated femur was further cultivated for 2 hours at 37° C. in 1 ml of fresh culture medium containing 1 μCi/ml of $^{45}CaCl_2$ to label the bone mineral with $^{45}Ca$. Then, the cultivated bone was rinsed with phosphate-buffered saline warmed at 37° C. to remove $^{45}Ca$ adhered to the bone. $^{45}Ca$-labelled bone was again cultivated using the roller-tube method, and the radioactivity of $^{45}Ca$ in an aliquot of the culture medium was determined with a liquid scintillation counter at points of 2, 24, 48 and 72 hours, respectively. The culture medium was freshened at each determination of the radioactivity. After completion of the cultivation, the bone was immersed in 1 ml of 1N HCl for 24 hours to elute all calcium in the bone, and the remaining radioactivity in the bone was determined.

The rate of remaining radioactivity in the bone to the initial radioactivity in the bone was measured from the obtained data at each observation. Then the eluting rate of bone mineral by osteoclasts was obtained by linear-regression of the decay curve for the rate of remaining radioactivity in the bone after 24 to 72 hours of the cultivation, and the turnover rate of calcium in the bone mineral accumulated in the cultivated bone was estimated as the biological half-life ($T_{1/2}$).

In the case that $T_{1/2}$ of the test compound group of the present invention preparations is larger than that of the control group, this shows that these compounds have an inhibitory effect on bone resorption. The potency of the inhibition of presented compounds was calculated by the following equation using $T_{1/2}$.

$$\text{Inhibitory potency on bone resorption} = \frac{T_{1/2} \text{ of the test compound group}}{T_{1/2} \text{ of the control group}}$$

The results are shown in the following table as the mean value of 5 observations.

| [Compounds] | [Inhibitory potency on bone resorption] |
|---|---|
| 1 | 3.56 |
| 2 | 1.15 |
| 3 | 1.42 |
| 4 | 2.90 |
| 5 | 1.04 |
| 6 | 1.29 |
| 7 | 1.69 |
| 8 | 2.12 |
| 10 | 1.22 |

EXAMPLE 8

Stimulatory effect on ossification

The stimulating effect of various compounds on ossification was tested according to the method described in "Advanced Tissue Cultures For In Vitro Assay And Production" (pages 103-111, edited by Isao Yamane & Hiroyoshi Endo, Published by SOFT SCIENCE, Inc. Tokyo).

Femur was isolated from a 9-day chick embryo. After cleaning off adherent soft tissues, one femur of a paired femora was used for a test of compound of a the present invention, and the other femur was used as a control. One preparation was placed directly on the inner surface of a glass roller-tube, and 2 ml of BGJb-HW2 culture medium was added to each tube. Each preparation was cultivated at 37° C. by the roller-tube method for 6 days. During the cultivation, femur length was measured, and the culture medium was freshened every other day. Each tested compound was dissolved in dimethylsulfoxide at a concentration of 0.01M and the solution was diluted by the culture medium to make a final concentration of a $10^{-5}M$ of those compounds. In the case of control group, the same volume of dimethylsulfoxide was added.

After completion of the cultivation, the bone was immersed in 1N HCl for 24 hours to elute all calcium in the bone, and the eluted calcium was determined a chelating method using orthocresolphthalein.

The potency of the stimulatory effect on ossification of the present compounds was calculated by the following equation.

$$\text{Stimulatory potency on ossification} = \frac{\text{Amount of calcium in the test compound group}}{\text{Amount of calcium in the control group}}$$

The results are shown in the following table as the mean value of 6 observations.

| [Compounds] | [Stimulatory potency on ossification] |
|---|---|
| 1 | 1.61 |
| 2 | 1.04 |
| 5 | 1.07 |
| 6 | 1.07 |
| 7 | 1.04 |
| 8 | 1.09 |
| 9 | 1.16 |
| 10 | 1.03 |

The potency of the effect on the growth of femoral length of the present compounds was calculated by the following equation.

$$\text{potency of the effect on the growth of femoral length} = \frac{\text{femoral length in the test compound group}}{\text{femoral length in the control group}}$$

The results are shown in the following table as the mean value of 6 observations.

| [Compounds] | [Potency on growth of femoral length] |
|---|---|
| 2 | 1.05 |
| 4 | 1.03 |
| 6 | 1.10 |
| 9 | 1.03 |

EXAMPLE 9

Tablets

10 Grams of 3-(2-dimethylaminoethoxy)-5H-benzofuro[3,2-c]quinolin-6-one were admixed with 95 g of lactose and 40 g of Indian corn starch and with 700 ml of a 5% aqueous solution of hydroxypropyl cellulose, and then dried. The dried mixture was admixed with 8 g of calcium carboxymethyl cellulose and 7 g of calcium stearate and the mixture was shaped into 1000 tablets.

What is claimed is:

1. A compound represented by the formula:

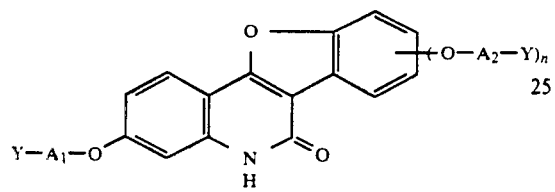

wherein $A_1$ and $A_2$ are the same, and represent a group of the formula $-CH_2)_m$ or $CH_2-CH(OH)CH_2-$, in which m represents an integer of from 1 to 3; Y represents an N,N-di-alkylamino group, an N-monoalkylamino group, a morpholino group or a 1-pyrrolidinyl group; n resents 0 or 1, and pharmaceutically acceptable acid addition salts thereof.

2. A compound, as claimed in claim 1 represented by the formula:

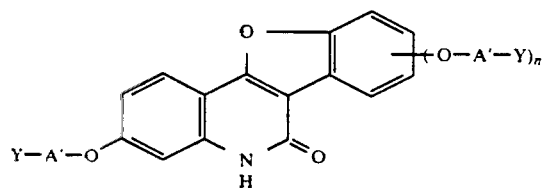

wherein A' represents a group of the formula of $-CH_2)_m$; Y represents an N,N-di-alkylamino group, an N-monoalkylamino group, a morpholino group or a 1-pyrrolidinyl group; n represents 0 or 1; m represents an integer of from 1 to 3, and pharmaceutically acceptable acid addition salts thereof.

3. A compound, as claimed in claim 1, represented by the formula:

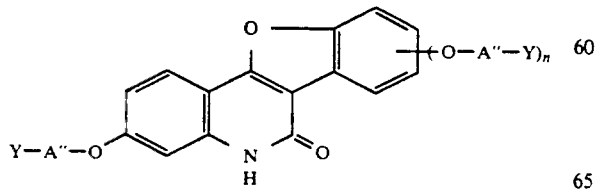

wherein A" represents a group of the formula of $-CH_2CH(OH)CH_2-$; Y represents an N,N-dialkylamino group, an N-mono-alkylamino group, a morpholino group or a 1-pyrrolidinyl group; n represents 0 or 1, and pharmaceutically acceptable acid addition salts thereof.

4. The compound, as claimed in claim 2, represented by the formula:

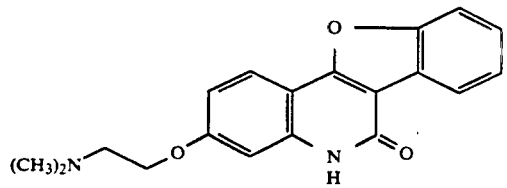

and the pharmaceutically acceptable acid addition salt thereof.

5. The compound, as claimed in claim 2, represented by the formula:

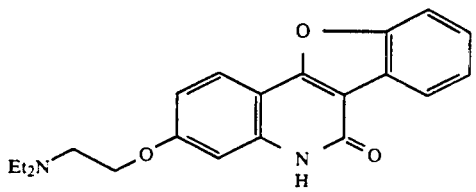

and the pharmaceutically acceptable acid addition salt thereof.

6. The compound, as claimed in claim 3, represented by the formula:

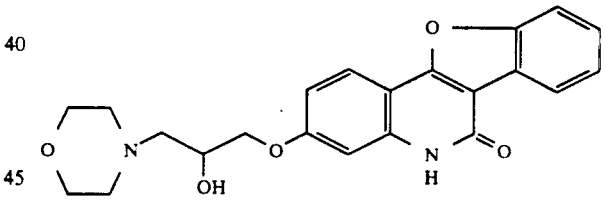

and the pharmaceutically acceptable acid addition salt thereof.

7. The compound, as claimed in claim 3, represented by the formula:

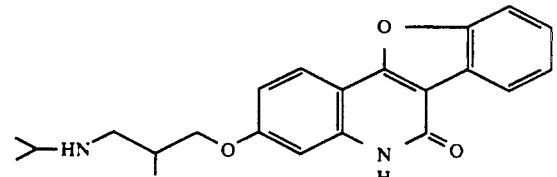

and the pharamceutically acceptable acid addition salt thereof.

8. A pharmaceutical composition for the prevention or treatment of osteoporosis comprising an inert pharmaceutical carrier and an effective amount of the compound represented by the formula:

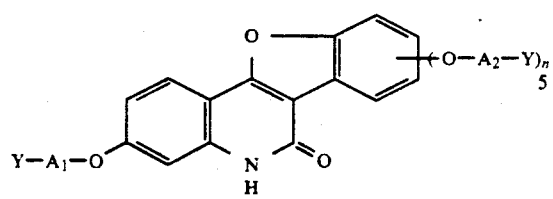

wherein $A_1$ and $A_2$ are the same, and represent a gorup of the formula $-(CH_2)_m$ or $-CH_2-CH(OH)CH_2-$, in which m represents an integer of from 1 to 3; Y represents an N,N-di-alkylamino group, an N-mono-alkylamino group, a morpholino group or a 1-pyrrolidinyl group; n represents 0 or 1, and pharmaceutically acceptable acid addition salts thereof.

9. A pharmaceutical composition, as claimed in claim 8, for the prevention or treatment of osteoporosis comprising an inert pharmaceutical carrier and an effetive amount of a compound represented by the formula:

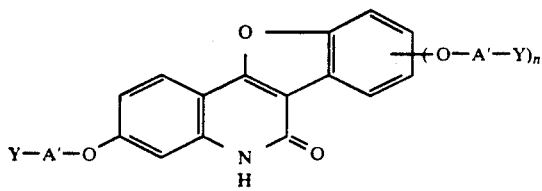

wherein A' represents a group of the formula of $-CH_2)_m$; Y represents an N,N-di-alkylamino group, an N-mono-alkylamino group, a morpholino group or a 1-pyrrolidinyl group; n represents 0 or 1; m represents an integer of from 1 to 3, and pharmaceutically acceptable acid addition salts thereof.

10. A pharmaceutical composition, as claimed in claim 8 for the prevention or treatment of osteoporosis comprising an inert pharmaceutical carrier and an effective amount of a compound represented by the formula:

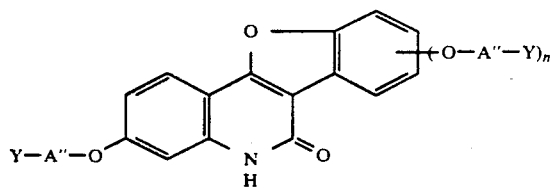

wherein A" represents a group of the formula of $-CH_2CH(OH)CH_2-$; Y represents an N,N-dialkylamino group, an N-mono-alkylamino group, a morpholino group or a 1-pyrrolidinyl group; n represents 0 or 1; and pharmaceutically acceptable acid addition salts thereof.

11. A pharmaceutically composition, as claimed in claim 9, for the prevention or treatment of osteoporosis comprising an inert pharmaceutical carrier and an effective amount of the compound represented by the formula:

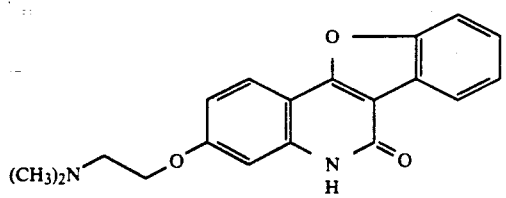

and the pharmaceutically acceptable acid addition salt thereof.

12. A pharmaceutical composition, as claimed in claim 9, for the prevention or treatment of osteoporosis comprising an inert pharmaceutical carrier and an effective amount of the compound represented by the formula:

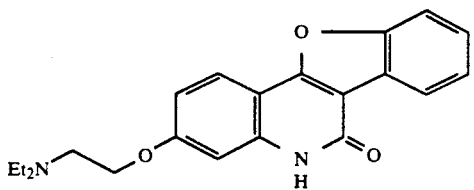

and the pharmaceutically acceptable acid addition salt thereof.

13. A pharmaceutical composition, as claimed in claim 10, for the prevention or treatment of osteoporosis comprising an inert pharmaceutical carrier and an effective amount of the compound represented by the formula:

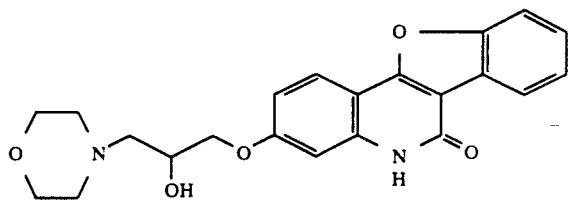

and the pharmaceutically acceptable acid addition salt thereof.

14. A pharmaceutical composition, as claimed in claim 10, for the prevention or treatment of osteoporosis comprising an inert pharmaceutical carrier and an effective amount of the compound represented by the formula:

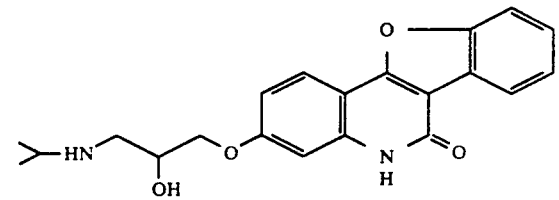

and the pharmaceutically acceptable acid addition salt thereof.

* * * * *